United States Patent
Flaherty

(10) Patent No.: US 7,662,110 B2
(45) Date of Patent: Feb. 16, 2010

(54) DEVICES FOR COLLECTING BLOOD AND ADMINISTERING MEDICAL FLUIDS

(75) Inventor: Patrice Flaherty, Minden, LA (US)

(73) Assignee: One Stick, LLC, Idalou, TX (US)

( * ) Notice: Subject to any disclaimer, the term of this patent is extended or adjusted under 35 U.S.C. 154(b) by 134 days.

(21) Appl. No.: 10/630,402

(22) Filed: Jul. 30, 2003

(65) Prior Publication Data

US 2005/0027233 A1 Feb. 3, 2005

(51) Int. Cl.
  A61B 5/00 (2006.01)
  A61B 5/02 (2006.01)
  A61B 19/00 (2006.01)
  B65D 81/00 (2006.01)
  A61M 37/00 (2006.01)
  A61M 29/00 (2006.01)
  A61M 31/00 (2006.01)
  G01N 1/00 (2006.01)

(52) U.S. Cl. ............... 600/576; 600/573; 600/575; 600/578; 600/579; 600/486; 73/863.85; 604/6.11; 604/6.12; 604/97.02; 604/6.16; 604/356; 604/500

(58) Field of Classification Search ............ 600/576, 600/573, 575, 578, 579, 486; 73/863.85; 604/6.11, 6.12, 97.02, 6.16, 356, 500
See application file for complete search history.

(56) References Cited

U.S. PATENT DOCUMENTS

| | | | | |
|---|---|---|---|---|
| 2,955,595 A * | 10/1960 | Semple | ............... | 600/573 |
| 3,782,382 A | 1/1974 | Naftulin et al. | ......... | 128/214 R |
| 4,186,752 A * | 2/1980 | Guerra | ............... | 600/579 |
| 4,187,860 A * | 2/1980 | Villari | ............... | 600/576 |
| 4,257,416 A * | 3/1981 | Prager | ............... | 604/507 |
| 4,447,235 A * | 5/1984 | Clarke | ............... | 604/167.02 |
| RE31,873 E | 4/1985 | Howes | ............... | 128/674 |
| 4,658,655 A * | 4/1987 | Kanno | ............... | 73/863.85 |
| 4,701,160 A * | 10/1987 | Lindsay et al. | ............... | 604/508 |
| 4,981,140 A * | 1/1991 | Wyatt | ............... | 600/486 |
| 5,059,168 A * | 10/1991 | Stone | ............... | 604/6.11 |
| 5,069,665 A * | 12/1991 | Ng | ............... | 604/97.02 |
| 5,084,034 A | 1/1992 | Zanotti | ............... | 604/319 |
| 5,089,421 A * | 2/1992 | Dieffenbach | ............... | 436/68 |
| 5,203,771 A | 4/1993 | Melker et al. | ............... | 604/53 |
| 5,364,377 A | 11/1994 | O'Neil | ............... | 604/283 |
| 5,395,347 A * | 3/1995 | Blecher et al. | ............... | 604/198 |

(Continued)

*Primary Examiner*—Max Hindenburg
*Assistant Examiner*—Jeffrey G Hoekstra
(74) *Attorney, Agent, or Firm*—R. Keith Harrison

(57) ABSTRACT

Novel devices which can be used to both collect blood samples from and administer medical fluids to a patient on a repeated and continual basis using one rather than multiple needle insertions. The device typically includes a main tubing segment confluently connected to a cannula for insertion in the patient's vein. A syringe port and a volumeter for collecting blood branch separately from the main tubing segment. The device is used to collect blood by attaching an empty blood collection syringe to the syringe port, inserting the cannula in the patient's vein, allowing passive flow of blood from the main tubing segment into the volumeter under intrinsic venous blood pressure and capillary action, and then facilitating active flow of blood from the volumeter into the blood collection syringe by extending the syringe plunger. The device may be used to administer medical fluids to the patient through the main tubing segment from a medical fluid syringe or catheter attached to the syringe port.

19 Claims, 3 Drawing Sheets

U.S. PATENT DOCUMENTS

| | | | |
|---|---|---|---|
| 5,396,899 A * | 3/1995 | Strittmatter | 600/576 |
| 5,486,159 A | 1/1996 | Mahurkar | 604/4 |
| 5,531,672 A * | 7/1996 | Lynn | 604/6.12 |
| 5,620,008 A * | 4/1997 | Shinar et al. | 600/576 |
| 5,772,608 A * | 6/1998 | Dhas | 600/578 |
| 5,772,625 A * | 6/1998 | Krueger et al. | 604/9 |
| 5,795,340 A | 8/1998 | Lang | 604/283 |
| 5,919,146 A * | 7/1999 | Propp | 600/577 |
| 5,961,472 A * | 10/1999 | Swendson et al. | 600/573 |
| 6,235,010 B1 * | 5/2001 | Wilkinson et al. | 604/356 |
| 6,413,228 B1 * | 7/2002 | Hung et al. | 600/562 |
| 6,485,428 B1 * | 11/2002 | Enk | 600/487 |
| 6,508,778 B1 | 1/2003 | Verkaart et al. | 604/6.15 |
| 2004/0082899 A1 * | 4/2004 | Mathias et al. | 604/6.16 |
| 2005/0096627 A1 * | 5/2005 | Howard | 604/500 |

* cited by examiner

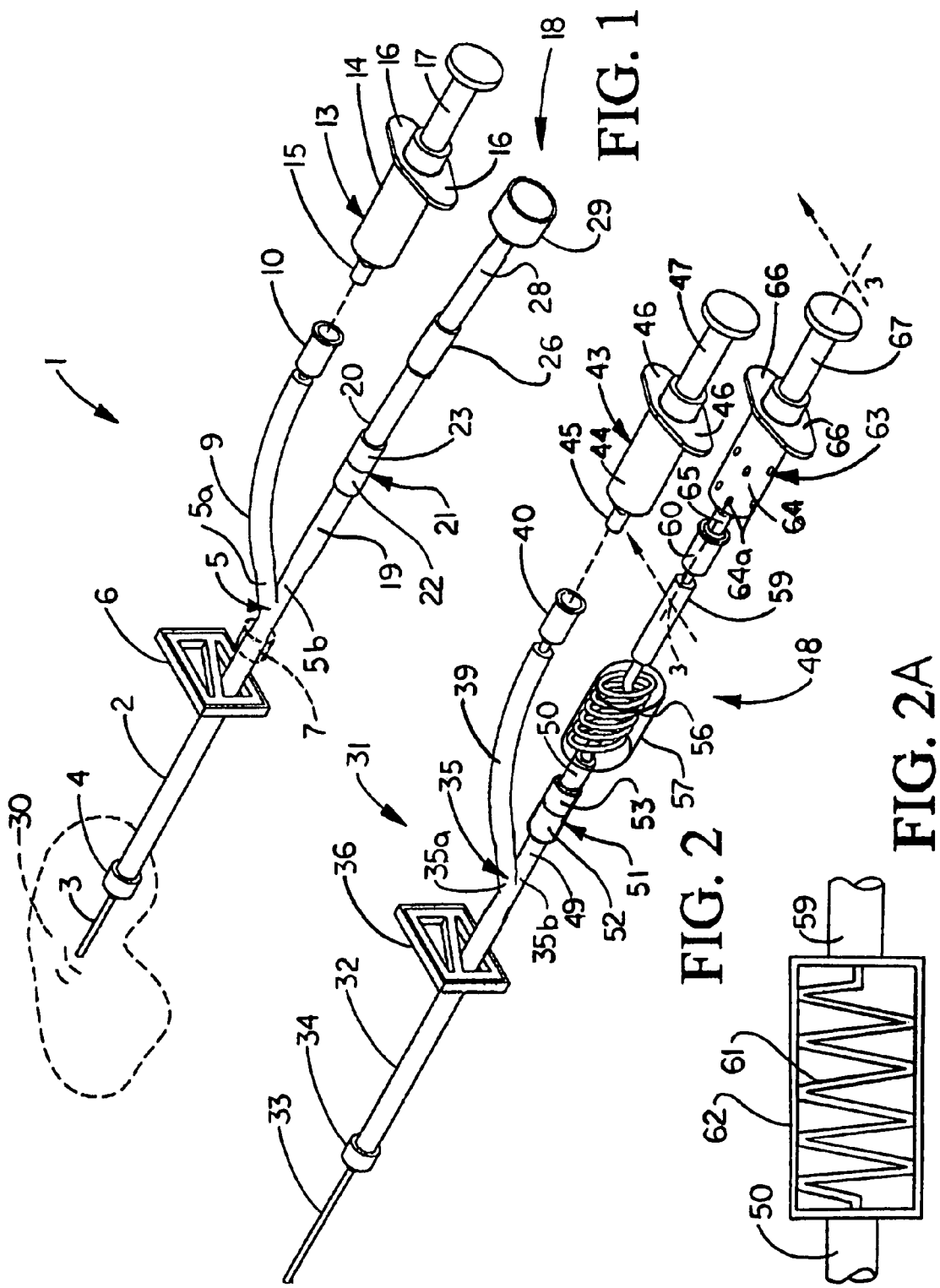

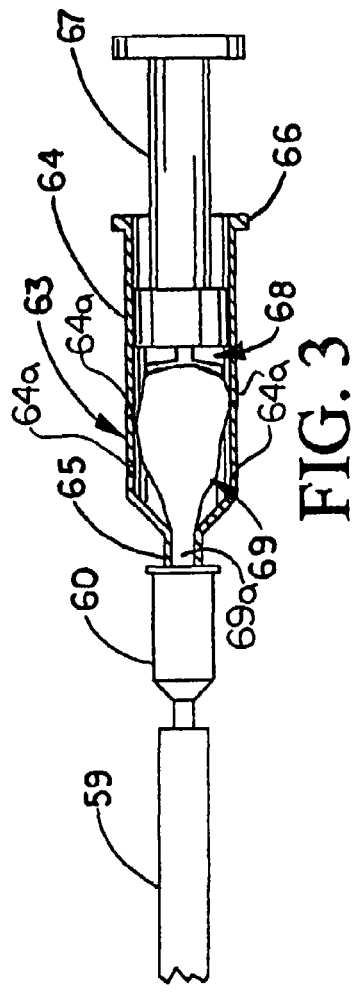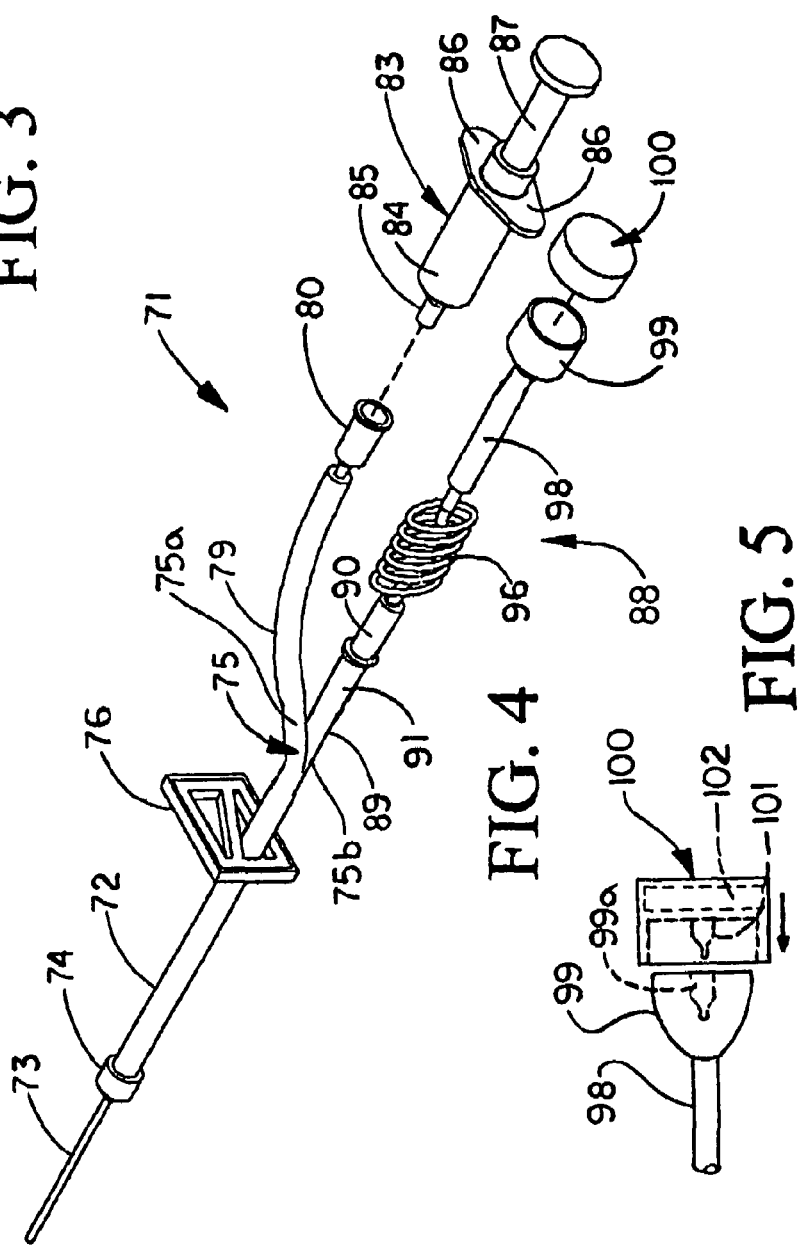

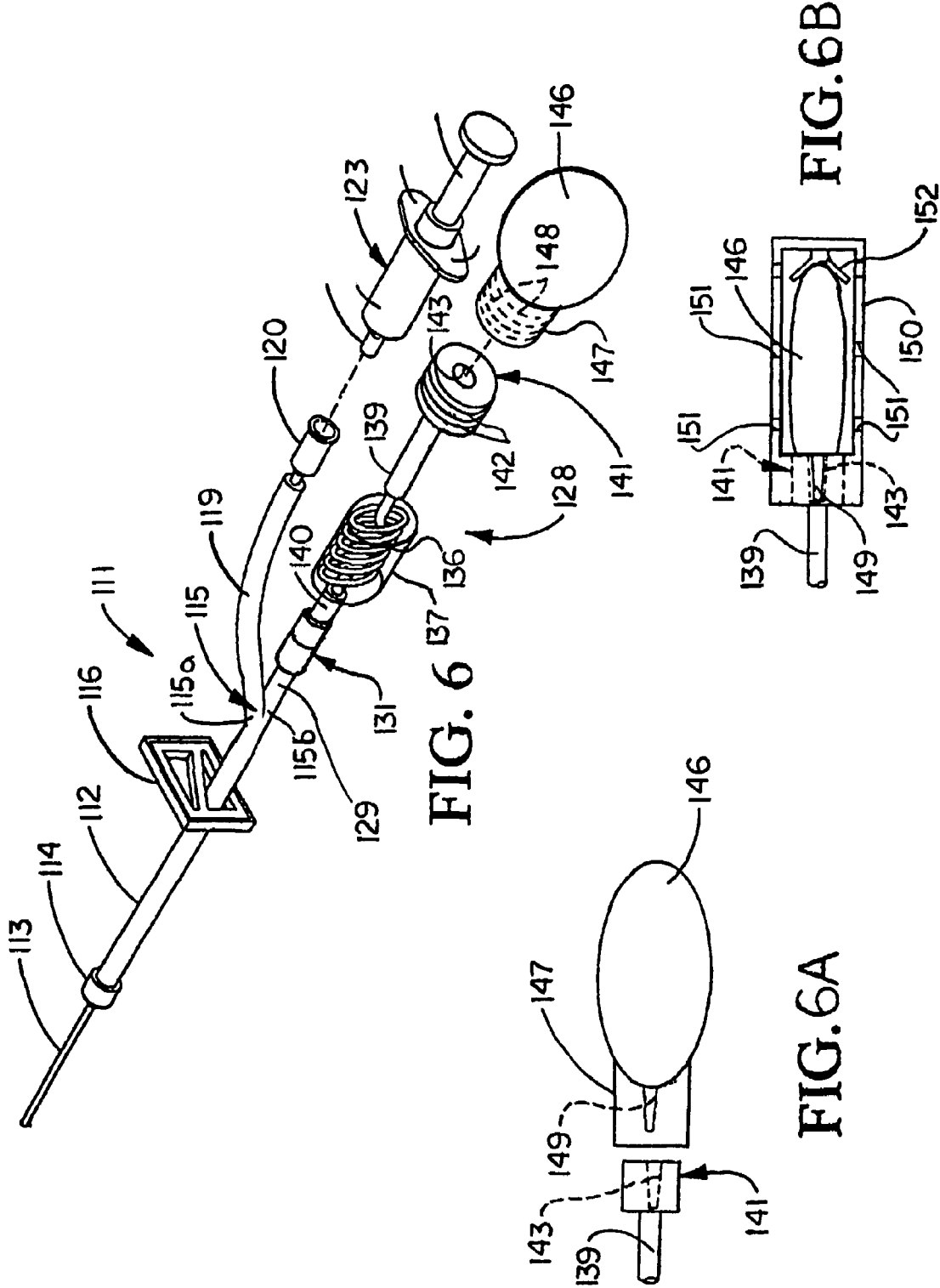

DEVICES FOR COLLECTING BLOOD AND ADMINISTERING MEDICAL FLUIDS

FIELD OF THE INVENTION

The present invention relates to syringes and other devices for removing blood from and administering medical fluids to a patient. More particularly, the present invention relates to novel devices which can be used to both collect blood from a patient and administer medicines and other medical fluids to the patient using a single needle insertion.

BACKGROUND OF THE INVENTION

Patients who undergo medical treatment in hospitals frequently require both extraction of blood for blood testing purposes and intravenous administration of medical fluids. Proper treatment of the patient may require that the blood be extracted and the medical fluids administered repeatedly and on a regular basis. In the past, this procedure has required that multiple needle insertions be made in various locations of the patient's body to access veins such as the external or internal jugular, subclavian, cephalic, femoral or saphenous veins. Multiple needle insertions not only result in considerable discomfort to the patient but also increase the risk of infection and compound the danger that medical personnel will be pricked by a contaminated needle.

Conventional methods of drawing blood from a patient typically utilize partial vacuum pressure to draw the blood from one of the patient's veins into a collecting device. Such utilization of partial vacuum pressure to draw blood from the vein tends to prematurely collapse the vein, thus necessitating re-insertion of the collecting device in another vein or in the same vein at a separate location to draw additional blood. This problem is particularly common in the drawing of blood from infants and the aged, in which small, thin veins are typically the source for blood samples. Accordingly, a device is needed which facilitates both collection of blood from and administration of medical fluids to a patient on a repeated basis using one, rather than multiple, needle insertions and which prevents premature collapse of a vein by utilizing intrinsic venous blood pressure to collect blood.

SUMMARY OF THE INVENTION

The present invention is generally directed to novel devices which can be used to both collect blood samples from and administer medical fluids to a patient on a repeated and continual basis using one rather than multiple needle insertions. The devices are capable of removing blood from one of the patient's veins using the intrinsic venous pressure of the blood and capillary action of the device, thereby preventing vacuum-induced collapse of the vein. The devices typically include a main tubing segment confluently connected to a cannula for insertion in the patient's vein. A syringe port and a device for estimating the rate of blood flow, hereinafter called a volumeter, branch separately from the main tubing segment. The device is used to collect blood by attaching an empty blood collection syringe to the syringe port, inserting the cannula in the patient's vein, allowing passive flow of blood from the main tubing segment into the volumeter under intrinsic venous blood pressure and capillary action, and then facilitating active flow of blood from the volumeter into the blood collection syringe by extending the syringe plunger. The blood-filled syringe may be replaced by additional empty blood collection syringes and the procedure repeated, as needed, depending on the quantity of blood to be collected. The device may be used to administer medical fluids to the patient by first drawing the residual blood from the main tubing segment and volumeter, flushing the main tubing segment with sterile normal saline and administering the fluids to the patient through the main tubing segment from a medical fluid syringe or catheter attached to the syringe port or to an auxiliary port connected to the main tubing segment.

In one embodiment, a membrane permeable to air, but not to liquid, is attached distal to the volumeter, which may be a chamber, an elongated folded or coiled tubing, or any other element which is capable of enabling visual estimation of the rate of blood flow toward the membrane. The syringe port branches from the main tubing segment and accepts a syringe to collect blood for tests. The volumeter may be removed from the device, leaving the syringe port available for accepting a medication-filled syringe for administration of medical fluids to the patient.

In another embodiment, a deformable reservoir is provided in fluid communication with the cannula and volumeter. The reservoir may be protected in the barrel of a syringe or other protective covering with vented openings along its barrel. After the blood-drawing procedure is completed using the blood collection syringe, residual blood may be effectively removed from the device by flushing the tubing with sterile normal saline. Removal of the reservoir unit from the device allows the remaining part of the device to be used as an ordinary "Y" tubing.

In another embodiment, a main tubing segment confluently connected to a cannula for insertion in the patient's vein. A syringe port and a device for estimating the rate of blood flow, hereinafter called a volumeter, branch separately from the main tubing segment. The device is used to collect blood by attaching an empty blood collection syringe to the syringe port, inserting the cannula in the patient's vein, allowing passive flow of blood from the main tubing segment into the volumeter under intrinsic venous blood pressure and capillary action, and then facilitating active flow of blood from the volumeter into the blood collection syringe by extending the syringe plunger. The blood-filled syringe may be replaced by additional empty blood collection syringes and the procedure repeated, as needed, depending on the quantity of blood to be collected. The device may be used to administer medical fluids to the patient by first drawing the residual blood from the main tubing segment and volumeter, flushing the main tubing segment with sterile normal saline and administering the fluids to the patient through the main tubing segment from a medical fluid syringe or catheter attached to the syringe port or to an auxiliary port connected to the main tubing segment. Additional embodiments are disclosed.

BRIEF DESCRIPTION OF THE DRAWINGS

The invention will now be described, by way of example, with reference to the accompanying drawings, in which:

FIG. 1 is a perspective view of an illustrative embodiment of the device of the present invention, with a cannula of the device inserted in a patient (in phantom);

FIG. 2 is a perspective view of another illustrative embodiment of the device of the present invention;

FIG. 2A is a side view of a folded tubing volumeter of the device of the present invention;

FIG. 3 is a cross-sectional view taken along section lines 3-3 in FIG. 2;

FIG. 4 is an exploded, perspective view of still another illustrative embodiment of the device of the present invention;

FIG. 5 is a side view of a port element of the device of FIG. 4 and a cap device removably engaging the port;

FIG. 6 is an exploded, perspective view of still another illustrative embodiment of the device of the present invention;

FIG. 6A is a side view of a port element of the device of FIG. 6 and a blood receptacle removably engaging the port; and FIG. 6B is a cross-section of a blood receptacle contained in a receptacle casing in another embodiment of the device of the present invention.

DETAILED DESCRIPTION OF THE INVENTION

Referring initially to FIG. 1 of the drawings, an illustrative embodiment of the device for collecting blood and administering medical fluids, hereinafter "device", of the present invention is generally indicated by reference numeral 1. The device 1 includes a main tubing segment 2 which is typically a flexible material. A hub 4 of a cannula 3 is threadibly or otherwise attached to the main tubing segment 2. A tubing bifurcation 5 is provided in the end of the main tubing segment 2 which is opposite or distal to the cannula 3, and the tubing bifurcation S may be continuous with or a separate element with respect to the main tubing segment 2. A tubing clamp 6 is provided on the main tubing segment 2 between the cannula hub 4 and the tubing bifurcation 5. The tubing clamp 6 may be any type of clamp which is capable of facilitating selective and reversible blocking of the flow of fluids through the main tubing segment 2. The tubing clamp 6 is preferably capable of one-handed operation.

A syringe tubing segment 9 extends from a syringe tubing leg 5a of the tubing bifurcation 5 and may be continuous with or a separate element with respect to the tubing bifurcation 5. A syringe port 10 is provided in the end of the syringe tubing 9 which is opposite the tubing bifurcation 5. The syringe port 10 may a needle-less syringe port such as a female luer-lock connector element or other type of threaded element known by those skilled in the art, or may be any type of threadless connector which is capable of providing reversible and secure fluid communication between a syringe 13 and the syringe tubing segment 9. The syringe 13 may be conventional and typically includes a cylindrical syringe barrel 14 having a syringe connector 15 such as a male luer-lock connector element, for example, or other structure which is capable of removably and securely engaging the companion syringe port 10. The syringe 13 typically further includes barrel flanges 16 and an extendible and retractable syringe plunger 17.

A collector tubing segment 19 extends from a collector tubing leg 5b of the tubing bifurcation 5 and may be continuous with or a separate element with respect to the tubing bifurcation 5. An indicator unit 18 of the device 1 includes a volumeter tubing segment 20 which is provided in fluid communication with the collector tubing segment 19. The indicator unit 18 may be removably attached to the collector tubing segment 19 by a tubing connector 21, which may include a receiver element 22 provided on the collector tubing 19 and an insertion element 23 provided on the volumeter tubing segment 20, as shown. When it is inserted in the receiver element 22, the insertion element 23 defines a fluid-sealed end of the indicator unit 18 in which fluid is incapable of escaping from the interior to the exterior of the indicator unit 18 through the tubing connector 21. Alternatively, the receiver element 22 may be provided on the volumeter tubing segment 20 and the insertion element 23 may be provided on the collector tubing segment 19. When provided on the collector tubing segment 19, the receiver element 22 may be a syringe port adapted for removably receiving a syringe for the administration of medical fluids to a patient, as hereinafter further described. It is understood that the indicator unit 18 may be fixedly rather than removably attached to the collector tubing segment 19. Further in the alternative, a connector 7 (in phantom) may be provided between the clamp 6 and the bifurcation 5 to facilitate disconnecting the syringe tubing segment 9 and syringe port 10, together with the connected indicator unit 18, from the main tubing segment 2, in order to discard the syringe tubing segment 9 and indicator unit 18, as desired.

The indicator unit 18 may further include a volumeter 26, which is typically a volumeter chamber and made of a transparent material, provided in the volumeter tubing segment 20. Alternatively, the volumeter 26 may be an elongated segment of transparent coiled or folded tubing, as hereinafter described with respect to FIGS. 2, 2A and 4. Membrane tubing 28 of the indicator unit 18 extends from the volumeter 26, and an air-permeable membrane 29 is provided on the membrane tubing 28. The air-permeable membrane 29 is preferably impermeable to liquids and may be any structure which is capable of facilitating bidirectional flow of air in the membrane tubing 28 toward the membrane 29 or bidirectional flow of air between the volumeter chamber 26 and the membrane tubing 28 while preventing the flow of blood out from the membrane tubing 28.

Referring again to FIG. 1, in typical use, the device 1 is initially used to remove blood from a subcutaneous vein of a patient 30 for blood sampling purposes. Accordingly, the clamp 6 is adjusted to the closed position to seal the main tubing segment 2 between the cannula 3 and the tubing bifurcation 5. The tubing connector 21 is inspected to ensure an airtight and fluid-tight connection between the collector tubing segment 19 and the volumeter tubing segment 20 of the indicator unit 18. With the main tubing segment 2, the syringe tubing segment 9, the collector tubing segment 19 and the indicator unit 18 containing air, the cannula 3 is inserted into the vein of the patient 30 through the skin, as shown. The cannula 3 is typically taped in place to immobilize the device 1 on the patient 30.

After the syringe connector 15 of the syringe 13 is attached to the syringe port 10 of the syringe tubing segment 9, the clamp 6 is adjusted to open the main tubing segment 2. Accordingly, as blood flows from the vein of the patient 30 through the cannula 3 and the main tubing segment 2, air is displaced by the advancing blood from the main tubing segment 2, the collector tubing segment 19 and the indicator unit 18, respectively, toward the membrane 29. Due to the resulting air pressure in the collector tubing segment 19 being low relative to the higher venous pressure in the main tubing segment 2, the blood flows from the main tubing segment 2 and collector tubing leg 5b of the tubing bifurcation 5, into the collector tubing segment 19 and does not enter the syringe tubing segment 9. Blood continues to flow from the main tubing segment 2 and collector tubing segment 19, through the tubing connector 21 and volumeter tubing segment 20, respectively, of the indicator unit 18 and enters and collects in the volumeter chamber 26. Next, the syringe plunger 17 is slowly extended from the syringe barrel 14 of the blood collecting syringe 13 to initially draw air from the syringe tubing segment 9 and into the syringe barrel 14 of the syringe 13, thereby inducing a drop in air pressure inside the syringe tubing segment 9 relative to both the pressure in the collector tubing segment 19 and the intrinsic venous pressure in the main tubing segment 2. This pressure drop causes blood to flow from the volumeter chamber 26, the volumeter tubing segment 20 and the collector tubing segment 19, respectively, and enter the syringe tubing segment 9 and then the syringe barrel 14 of the syringe 13.

As the syringe plunger 17 is slowly pulled from the syringe barrel 14, care is taken to avoid pulling the syringe plunger 17 at a rate which causes the blood supply in the volumeter chamber 26 to be depleted and the air/blood interface to advance through the collector tubing segment 19 and beyond the tubing bifurcation 5, in which case air would be drawn from the collector tubing segment 19 and into the syringe tubing segment 9, and thus into the collecting syringe 13. This extension of the plunger 17 from the syringe barrel 14 at a relatively slow, controlled rate ensures that blood is extracted from the vein of the patient 30 and into the device 1 using the intrinsic flow pressure of the blood in the vein and prevents application of vacuum pressure to the vein which would tend to collapse the vein and hinder further flow of blood therefrom, as well as prevents or minimizes hemolysis of red blood cells in the extracted blood. Typically, the syringe plunger 17 is pulled from the syringe barrel 14 at a rate which is sufficient to facilitate maintaining a substantially constant volume of blood in the volumeter chamber 26 as blood continues to be obtained from the main tubing segment 2, through the syringe tubing segment 9 and into the blood collection syringe 13. This is ensured by keeping the air/fluid interface distal to the bifurcation 5 and proximal to the membrane 29, facilitated by a visual assessment of the blood flow rate provided by the volumeter chamber 26. It is understood that the volumeter 26 may be omitted from the indicator unit 18, in which case the indicator unit 18 may be a segment of clear tubing or any other element which is capable of enabling a user of the device 1 to visually inspect the progress of blood flow therethrough and prevent the air/fluid interface from passing beyond the bifurcation 5 to the syringe tubing segment 9 while obtaining the blood sample.

After the desired volume of blood has been collected in the syringe barrel 14, the tubing clamp 6 is adjusted to block further flow of blood through the main tubing segment 2. With the tubing clamp 6 remaining in the closed position, the syringe plunger 17 of the syringe 13 is extended from the syringe barrel 14 until all residual blood has been drawn from the indicator unit 18, the collector tubing segment 19 and the syringe tubing segment 9, and into the syringe barrel 14. Simultaneously, air is drawn through the indicator unit 18 through the membrane 29, the collector tubing segment 19 and the syringe tubing segment 9, respectively, until these elements are filled with air. The blood-filled syringe 13 is then removed from the device 1 by disconnecting the syringe connector 15 from the syringe port 10, and the blood collected in the syringe 13 is subjected to blood testing. Additional blood samples may be collected in an additional syringe or syringes, as needed, by attaching each additional empty syringe 13 to the syringe tubing segment 9 at the syringe port 10 and collecting the additional samples of blood in the syringe 13 or successive syringes 13, in the manner heretofore described.

After the blood sample or samples is/are collected, the device 1 may be used to administer medical fluids to the patient 30, as follows. A syringe 13, the barrel 14 of which contains a supply of saline flush solution, is initially attached to the syringe port 10. As the syringe plunger 17 is subsequently depressed into the fluid-filled syringe barrel 14, the saline solution is ejected therefrom and flows through the syringe tubing segment 9, the collector tubing segment 19, the volumeter tubing segment 20 and into the volumeter chamber 26, respectively. The volumeter tubing segment 20 may then be disconnected from the collector tubing segment 19 at the tubing connector 21 and discarded along with the volumeter chamber 26, the membrane tubing 28 and the membrane 29 of the indicator unit 18, as desired. The tubing clamp 6 is then again adjusted to the open position and depression of the syringe plunger 17 into the syringe barrel 14 is continued to flush the main tubing segment 2 with saline flush solution. The syringe 13 is then removed and a replacement syringe 13 containing a fluid medication or a catheter (not shown) connected to an IV bag (not shown) may then be attached to the syringe port 10 for the administration of medical fluids to the patient 30 through the syringe tubing segment 9, or alternatively, through the syringe port 22, the collector tubing segment 19 and the main tubing segment 2, respectively.

In the event that additional blood samples from the patient 30 are required after administration of the medical fluids from the syringe 13 has begun or been completed, and fluid contents of the syringe 13 are expelled into the syringe tubing segment 9, the tubing clamp 6 is adjusted to the closed position. A replacement indicator unit 18 may then be attached to the collector tubing segment 19 at the tubing connector 21. The plunger 17 of syringe 13, emptied of the medical fluid contents, is then extended to draw residual medical fluids from the indicator unit 18 and syringe tubing segment 9, and the syringe 13 is removed from the syringe port 10 and discarded. The clamp 6 is now opened, allowing fluid from main tubing segment 2 to flow toward membrane 29. Plunger 17 is further extended recovering any saline/blood mix. The clamp 6 is then closed, and another empty blood-collecting syringe 13 is connected to the syringe port 10, the tubing clamp 6 is again adjusted to the open position, and the syringe 13 is used to obtain the additional blood from the patient 30, respectively, as heretofore described.

Referring next to FIGS. 2, 2A and 3 of the drawings, another illustrative embodiment of the device of the present invention is generally indicated by reference numeral 31 and includes a main tubing segment 32, to one end of which is securely connected a hub 34 of a cannula 33. A tubing bifurcation 35 is provided in the opposite end of the main tubing segment 32 and defines a syringe tubing leg 35a and an adjacent collector tubing leg 35b. A tubing clamp 36 of selected design is provided on the main tubing segment 32, between the cannula hub 34 and the tubing bifurcation 35. Preferably, the tubing clamp 36 is capable of one-handed operation.

A syringe tubing segment 39 extends from the syringe tubing leg 35a of the tubing bifurcation 35. A syringe port 40, which is typically a needle-less luer-lock connector, for example, is provided in the end of the syringe tubing 39 which is distal to the tubing bifurcation 35. A syringe 43, typically including a cylindrical syringe barrel 44 having a syringe connector 45 such as a male luer-lock connector element, for example, removably engages the syringe port 40 in fluid-tight connection therewith. The blood collection syringe 43 may be conventional and typically further includes barrel flanges 46 and an extendible and retractable syringe plunger 47.

A collector tubing segment 49 extends from the collector tubing leg 35b of the tubing bifurcation 35. A indicator unit 48 may be removably connected to the collector tubing segment 49 at a tubing connector 51, and a protective container such as a covering syringe 63 may be removably connected to the indicator unit 48 for purposes which will be hereinafter described. The indicator unit 48 may include a volumeter 56 which is typically provided between a port tubing segment 59 and a volumeter tubing segment 50 and may be encased in a transparent volumeter casing 57. The tubing connector 51 may include a receiver element 52 which is typically provided on the collector tubing segment 49 and removably receives an insertion element 53 typically provided on the volumeter tubing segment 50. Alternatively, the receiver element 52 may be provided on the volumeter tubing segment 50 and the insertion element 53 provided on the collector tubing segment 49. The volumeter 56 is typically a clear, transparent device having an elongated, generally spiral configuration, as shown in FIG. 2. However, it is understood that the volumeter 56 may alternatively be a volumeter chamber such as the volumeter chamber 26 heretofore described with respect to FIG. 1. Still further in the alternative, as shown in FIG. 2A, the volumeter 61 may be configured as a folded volumeter tubing that is folded into a zigzag pattern in a transparent volumeter casing 62.

A syringe port 60, which may be a needle-less female luer-lock connector, for example, is provided on the port tubing segment 59 of the indicator unit 48. As shown in FIG. 3, a residual blood collection reservoir 69 typically may be covered by a syringe barrel 64 of a protective container such as the covering syringe 63 having a syringe connector 65 which may be a male luer-lock connector element, for example, for removable connection to the companion syringe port 60. The protective covering syringe 63 may include a pair of barrel flanges 66 extending from the syringe barrel 64 and a syringe plunger 67 slidably disposed in the barrel interior 68 (FIG. 3) of the syringe barrel 64.

As shown in FIGS. 2 and 3, one or more barrel openings 64a extend through the wall of the syringe barrel 64. As shown in FIG. 3, the blood-collecting reservoir 69 is provided in the barrel interior 68 of the syringe barrel 64. The reservoir 69 may be a very thin, easily deformable balloon-type structure, which is typically partially collapsed and is provided in fluid communication with the cannula 33 and volumeter 56. The reservoir 69 is formed typically of a thin plastic material or a rubber material or other easily deformable material that allows the interior volume of the reservoir 69 to be maintained a: ambient air pressure. The reservoir 69 includes an intake end 69a which is typically secured in the syringe connector 65 and has an intake opening (not shown) which faces the syringe port 60. The distal end of the reservoir 69 is affixed to the plunger 67, as shown in FIG. 3. In operation of the device 31 as hereinafter described, the reservoir 69 is designed to receive residual blood from the volumeter 56. By withdrawal of the syringe plunger 47 slowly from the syringe barrel 44 of the syringe 43, blood is drawn from the reservoir 69; through the volumeter 56, the collector tubing segment 49 and the syringe tubing segment 39, respectively; and into the syringe barrel 44 of the syringe 43. The indicator unit 48 can then be removed from the collector tubing segment 49 at the tubing connector 51 and discarded.

In typical use the device 31 is initially used to obtain blood from a subcutaneous vein of a patient (not shown) and may thereafter be used to administer medical fluids to the patient, as heretofore described with respect to the device 1 of FIG. 1. Accordingly, the clamp 36 is adjusted to the closed position to seal the main tubing segment 32 between the cannula 33 and the tubing bifurcation 35; the cannula 33 is inserted into the vein of the patient; the syringe connector 45 of the blood collection syringe 43 is attached to the syringe port 40 of the syringe tubing segment 39; and the clamp 36 is adjusted to open the main tubing segment 32. As blood flows from the vein of the patient through the cannula 33 and into the main tubing segment 32, air is displaced by the advancing blood from the main tubing segment 32, the collector tubing segment 49, the indicator unit 48, and into the partially-collapsed blood collection reservoir 69 (FIG. 3). Due to the resulting air pressure in the collector tubing segment 49 being low relative to the higher venous pressure in the main syringe tubing 32 and therefore, facilitated by the expandable blood collection reservoir 69, the blood flows from the main tubing segment 32 and collector tubing leg 35b of the tubing bifurcation 35, into the collector tubing segment 49 and does not enter the syringe tubing segment 39. Blood continues to flow from the main tubing segment 32 and collector tubing segment 49, through the tubing connector 51 and volumeter tubing segment 50, respectively, and enters and collects in the volumeter 56. In the event that some of the blood flows from the volumeter 56 and through the port tubing segment 59 and the syringe port 60 and into the syringe connector 65 of the covering syringe 63, this blood is collected-in the blood collecting reservoir 69 (FIG. 3) and may later be expelled from the covering syringe 63 as an additional blood sample, as hereinafter further described.

After the blood has entered the volumeter 56 from the collector tubing segment 49, as heretofore described, the syringe plunger 47 of the blood collection syringe 43 is slowly extended from the syringe barrel 44 of the blood collecting syringe 43 to initially draw air from the syringe tubing segment 39 and into the syringe barrel 44 of the syringe 43, thereby inducing a drop in air pressure inside the syringe tubing segment 39 relative to the air pressure in the collector tubing segment 49. This causes blood to flow from the volumeter 56, the volumeter tubing segment 50 and the collector tubing segment 49, respectively, and enter the syringe tubing segment 39 and the syringe barrel 44 of the syringe 43.

As the syringe plunger 47 is slowly pulled from the syringe barrel 44 of the blood collection syringe 43, care is taken to avoid pulling the syringe plunger 47 at a rate which causes the blood supply in the volumeter 56 to be depleted and the air/blood interface to advance beyond the tubing bifurcation 35, in which case air would be drawn from the collector tubing segment 49 and into the syringe tubing segment 39. Typically, the syringe plunger 47 is pulled from the syringe barrel 44 at a rate which is sufficient to facilitate maintaining a substantially constant volume of blood in the volumeter 56 as blood continues to be obtained from the main tubing segment 32, through the collector tubing segment 49 and volumeter tubing segment 50, respectively, and into the volumeter 56. This extension of the plunger 47 from the syringe barrel 44 at a relatively slow, controlled rate ensures that blood is extracted from the vein of the patient and into the device 31 using the intrinsic flow pressure of the blood in the vein.

After the desired volume of blood has been collected in the syringe barrel 44 of the blood collection syringe 43, the tubing clamp 36 is adjusted to block further flow of blood through the main tubing segment 32. While the tubing clamp 36 remains in the closed position, the syringe plunger 47 of the blood collection syringe 43 is extended from the syringe barrel 44 until all residual blood has been drawn from the volumeter 56, the volumeter tubing segment 50, the collector tubing segment 49 and the syringe tubing segment 39, and into the syringe barrel 44. The blood-filled blood collection syringe 43 is then removed from the device 31 by disconnecting the syringe connector 45 from the syringe port 40, and the blood collected therein is subjected to blood testing. Additional blood samples may be collected in an additional blood collection syringe or syringes, as needed, by attaching each additional empty blood collection syringe 43 to the syringe tubing segment 39 at the syringe port 40 and collecting the additional samples of blood in the blood collection syringe 43 or successive blood collection syringes 43, as heretofore described. Any blood collected in the blood collection reservoir 69 (FIG. 3) may be collected in the barrel 44 of the blood collection syringe 43 by pulling the plunger 47 from the syringe barrel 44.

The device 31 may be used to administer medical fluids to the patient, as heretofore described with respect to the device 1 of FIG. 1 and as follows. After removal of the blood-filled blood collecting syringe 43 from the syringe port 40, a replacement syringe 43, the barrel 44 of which contains a supply of sterile normal saline flush solution, is securely attached to the syringe port 40. The syringe plunger 47 is then depressed into the syringe barrel 44 to force the saline solution through the syringe tubing segment 39; the collector tubing segment 49; the volumeter tubing segment 50, the volumeter 56 and the port tubing segment 59 of the indicator unit 48; and into the blood collection reservoir 69 (FIG. 3), respectively. The indicator unit 48 may then be disconnected from the collector tubing segment 49 at the tubing connector 51 and discarded along with the residual blood collection reservoir 69 encased in the covering syringe 63. Alternatively, any blood/saline mix remaining in the reservoir 69 may be used for blood culture by allowing partial vacuum test tube or bottle to pull specimen into appropriate container. The tubing clamp 36 is then again adjusted to the open position and depression of the syringe plunger 47 into the syringe barrel 44 is continued to flush the main tubing segment 32 with saline flush solution. The syringe 43 is then removed and a replacement syringe 43 containing a fluid medication or a catheter (not shown) connected to an IV bag (not shown) may then be attached to the syringe port 40 for the administration of medical fluids to the patient through the syringe tubing segment 39 and the main tubing segment 32, respectively. Additional blood samples may be obtained from the patient by removing the medical fluid-filled syringe 43 from the syringe port 40, connecting a replacement indicator unit 48 and residual blood collection reservoir 69 to the collector tubing segment 49, and connecting an empty blood-collecting syringe 43 to the syringe port 40 to obtain the blood from the patient, in the manner heretofore described.

Referring next to FIG. 4 of the drawings, still another illustrative embodiment of the device of the present invention is generally indicated by reference numeral 71 and includes a main tubing segment 72 to which a hub 74 of a cannula 73 is threadibly or otherwise attached. A tubing bifurcation 75 is provided in the end of the main tubing segment 72, and a tubing clamp 76 is provided on the main tubing segment 72. The tubing clamp 76 is preferably capable of one-handed operation.

A syringe tubing segment 79 extends from a syringe tubing leg 75a of the tubing bifurcation 75, and a syringe port 80 is provided in the end of the syringe tubing 79. A syringe 83 which may be conventional typically includes a cylindrical syringe barrel 84 having a syringe connector 85 such as a male luer-lock connector element, for example, or other structure which removably engages the syringe port 80. The syringe 83 typically further includes barrel flanges 86 and an extendible and retractable syringe plunger 87.

A collector tubing segment 89 extends from a collector tubing leg 75b of the tubing bifurcation 75. A syringe port 91, which may be a female luer-lock connector element, for example, is provided on the collector tubing segment 89. An indicator unit 88 includes a volumeter tubing segment 90 having a connector element (not shown) such as a male luer-lock connector which is removably connected to the syringe port 91. The indicator unit 88 typically further includes a blood volumeter 96 which may be a transparent coiled or folded tubing as shown and heretofore described with respect to the volumeter 56 of the device 31 of FIG. 2. Alternatively, the blood volumeter 96 may be a volumeter chamber such as the volumeter chamber 26 heretofore described with respect to FIG. 1. A membrane tubing segment 98 of the indicator unit 88 extends from the volumeter 96, and an self-sealing or other port 99 having a port receptacle 99a is provided on the tubing segment 98. Additionally, a cap device 100, preferably comprised of a distal air permeable membrane 102 and a proximal needle-less blunt probe or a protected needle 101, is capable of being attached securely to the port 99. It will be appreciated from a consideration of FIG. 5 that attachment of the cap device 100 to the port 99 causes the needle protected or needle-less probe 101 to be inserted into the receptacle 99a of the self-sealing port 99, and toward the membrane tubing segment 98. This will ensure that ambient outside pressure is allowed through the membrane 102 and into the membrane tubing segment 98. Since the intrinsic vein pressure is higher than ambient air pressure, blood will then flow toward the cap device 100. The air-permeable membrane 102 is preferably impermeable to liquids and may be any structure which is capable of facilitating flow of air from the volumeter 96 and the membrane tubing 98 while preventing the flow of blood from the membrane tubing 98. The exterior surface of the cap device 100 may be provided with cap threads (not shown) which engage interior cap threads (not shown) of the port 99 to secure the membrane cap device 100 on the port 99. Alternatively, the cap device 100 may be securely attached to the port 99 using any other suitable technique known by those skilled in the art.

In use, the device 71 may be used to obtain blood samples from a patient into one or multiple blood collection syringes 83 successively connected to the syringe port 80. After all blood samples have been obtained at the port 80, the tubing is then flushed with sterile normal saline solution in the same manner as heretofore described with respect to the syringe 13 of the device 1 of FIG. 1 and the syringe 43 of the device 31 of FIG. 2. Medical fluids may then be introduced into the patient using a fluid-filled syringe or successive fluid-filled syringes 83 in the same manner as heretofore described with respect to the device 1 of FIG. 1 and the device 31 of FIG. 2. In addition, the indicator unit 88 of the device 71 may be removed from the syringe port 91 of the device 71 and a syringe (not shown) or IV catheter (not shown) may be connected to the syringe port 91 for the introduction of medical fluids into the patient along with the medical fluids introduced into the device 71 through the syringe tubing segment 79 using the syringe 83 or successive syringes 83 filled with medical fluid.

Referring next to FIGS. 6-6B, another illustrative embodiment of the device of the present invention is generally indicated by reference numeral 111 and includes a main tubing segment 112 to which is attached a hub 114 of a cannula 113. A collector tubing segment 129 extends from the main tubing segment 112. A tubing clamp 116, which is preferably capable of one-handed operation, is provided in the main tubing segment 112. A collection unit 128 includes a volumeter tubing segment 140 which is provided in fluid communication with the collector tubing segment 129. The collection unit 128 may be removably attached to the collector tubing segment 129 by a tubing connector 131 of selected design.

The collection unit 128 typically further includes a volumeter 136 that may be contained inside a volumeter casing 137. A port tubing segment 139 extends from the volumeter 136, and a port 141 is provided on the distal end of the port tubing segment 139. The port 141 may be a needle-less port or a protective needle port, for example, known by those skilled in the art. As shown in FIG. 6A, a port opening 143 extends into the port 141 for removably receiving a companion receptacle connector 149 that extends from an inlet end of a collapsible and expandable blood receptacle 146. The blood receptacle 146 may be made of thin plastic, rubber or other deformable material and has a volume of typically from about ½ cc to about 10 cc, depending on laboratory requirements and the type of blood test to be conducted. As further shown in FIG. 6A, the blood receptacle 146 may be attached to an attachment sleeve 147 into which the receptacle connector 149 extends. As shown in FIG. 6, the port 141 may be provided with exterior port threads 142 that engage interior sleeve threads 148 provided in the attachment sleeve 147 to removably attach the blood receptacle 146 in fluid communication with the port 141. However, it is understood that the attachment sleeve 147 may be attached to the port 141 using any of a variety of alternative techniques known by those skilled in the art. For larger-sized blood receptacles 146 in which the quantity of blood to be collected therein is greater than typically about 1 cc, the blood receptacle 146 may be provided inside a receptacle casing 150 having one or more casing openings 151. The distal end of the blood receptacle 146 is attached or tethered to the receptacle casing 150 using an enclosure anchor 152.

As further shown in FIG. 6, a tubing bifurcation 115 may be provided in the distal end of the main tubing segment 112, in which case a syringe tubing segment 119 extends from a syringe tubing leg 115a of the tubing bifurcation 115 and the collector tubing segment 129 extends from a collector tubing leg 115b of the tubing bifurcation 115. A syringe port 120 is provided in the distal end of the syringe tubing 119 and removably receives a syringe 123 to obtain blood samples from and/or administer medical fluids to a patient, as hereinafter described. Additionally, the blood receptacle 146 is be used to collect blood samples from a patient for subsequent testing of the blood samples and then removed from the port 141 for testing of the blood samples. A syringe (not shown) or catheter can then be attached to the port 141 for the administration of medical fluids to the patient, as hereinafter further described.

In typical use, the cannula 113 is inserted into a subcutaneous vein (not shown) of a patient and the device 111 is taped in place. Because venous blood pressure inside the accessed vein is higher than ambient air pressure applied to the exterior of the blood receptacle 146, blood flows from the vein though the main tubing segment 112, the collector tubing segment 129 and the volumeter 136, respectively, and enters the blood receptacle 146. After the blood receptacle 146 is filled to capacity with blood, the attachment sleeve 147 is removed from the port 141 and additional empty blood receptacles 146 can be successively attached to the port 141 to obtain additional blood samples, as needed, which blood receptacles 146 may be sized according to the blood tests desired. After all blood specimens are collected, last blood receptacle 146 is removed from the port 141 and discarded, thereby exposing the self-sealing port 141. Normal saline is then used to flush the device 111 typically through the port 141, and an IV line (not shown) may be connected to the port 141, after which the device 111 is used as ordinary extension tubing. Alternatively, the device 111 can be flushed with sterile normal saline and the medical fluids can be administered to the patient using a syringe 123 or IV line connected to the syringe port 120, as heretofore described with respect to the embodiments of FIGS. 1-4.

During blood sampling, in the event that the cannula 113 is inserted in a large vein, blood typically flows rapidly into the blood receptacle 146, and therefore, the syringe 123 is not needed to obtain the blood samples. On the other hand, in the event that the cannula 113 is inserted in a small vein, blood typically flows slowly into the blood receptacle 146, and thus, the syringe 123 can be used instead to obtain the blood samples through the syringe port 120. A replacement syringe 123 or IV line (not shown) can then be attached to the port 120 for the administration of medical fluids to the patient through the syringe tubing segment 119. Accordingly, the syringe tubing segment 119, bifurcation 115, and syringe port 120 are optional components and can optionally be omitted from the device 111, as desired, since the port 141 is suitable for both obtaining blood samples from and administering medical fluids to the patient. Furthermore, the volumeter 136 is an optional element designed to assist the user in estimating the quantity of blood flowing from the main tubing segment 112 and into the receptacle 146, in use of the device 111.

While the preferred embodiments of the invention have been described above, it will be recognized and understood that various modifications can be made in the invention and the appended claims are intended to cover all such modifications which may fall within the spirit and scope of the invention.

Having described my invention with the particularity set forth above, I claim:

1. A device for collecting blood from and administering medical fluids to a patient, comprising:
    a main tubing segment for conveying the blood and the medical fluids;
    an indicator unit and an access port disposed in bidirectional fluid communication with said main tubing segment in branched relationship to each other at a tubing branch, said indicator unit adapted for indicating blood volume;
    wherein said indicator unit has a fluid-sealed first end disposed in fluid communication with and proximate said main tubing segment, a second end distal to said main tubing segment relative to said first end, an air flow pathway defined through said indicator unit between said first end and said second end and a bidirectional liquid flow pathway defined in coinciding relationship with said air flow pathway between said first end and said second end;
    a clamp operably engaging said main tubing segment and adapted to selectively block and unblock flow of the fluids in both directions through said main tubing segment; and
    at least one air-permeable and liquid-impermeable membrane provided at said second end of said indicator unit.

2. The device of claim 1 further comprising a blood volumeter provided in said indicator unit.

3. The device of claim 2 wherein said blood volumeter is a volumeter chamber.

4. The device of claim 3 wherein said indicator unit is disposed in removable fluid communication with said main tubing segment.

5. The device of claim 1 wherein said indicator unit is disposed in removable fluid communication with said main tubing segment.

6. The device of claim 5 further comprising a blood volumeter provided in said indicator unit.

7. A device for collecting blood from and administering medical fluids to a patient, comprising:
    a main tubing segment for conveying the blood and the medical fluids;
    a blood volumeter having a fluid-sealed first end disposed in fluid communication with and proximate said main tubing segment and a second end distal to said main tubing segment relative to said first end and an access port disposed in fluid communication with said main tubing segment in branched relationship to said blood volumeter, said blood volumeter adapted for indicating blood volume and said blood volumeter and said access port defining branched bidirectional fluid flow pathways;

wherein an air flow pathway is defined through said blood volumeter between said first end and said second end and a bidirectional liquid flow pathway coincides with said air flow pathway between said first end and said second end;

a clamp operably engaging said main tubing segment and adapted to selectively block and unblock flow of the fluids in both directions through said main tubing segment; and at least one air-permeable and liquid-impermeable membrane disposed in fluid communication with said blood volumeter at said second end of said blood volumeter and allowing bidirectional fluid movement between said blood volumeter and said access port.

8. The device of claim 7 wherein said blood volumeter is disposed in removable fluid communication with said main tubing segment.

9. The device of claim 7 wherein said blood volumeter is a volumeter chamber.

10. The device of claim 9 wherein said indicator unit is disposed in removable fluid communication with said main tubing segment.

11. A device for collecting blood from and administering medical fluids to a patient, comprising:

a main tubing segment for conveying the blood and the medical fluids;

an indicator unit having a fluid-sealed first end disposed in fluid communication with and proximate said main tubing segment, a second end distal to said main tubing segment relative to said first end, an air flow pathway extending through said indicator unit between said first end and said second end and a bidirectional liquid flow pathway coinciding with said air flow pathway between said first end and said second end;

an access port disposed in bi-directional fluid communication with said main tubing segment in branched relationship to said main tubing segment and said indicator unit at a tubing branch, said indicator unit having a blood volumeter between said first end and said second end of said indicator unit and adapted for indicating blood volume and said indicator unit and said access port defining branched bi-directional fluid flow pathways;

a clamp operably engaging said main tubing segment and adapted to block and unblock flow of the fluids in both directions through said main tubing segment;

at least one air-permeable and liquid-impermeable membrane provided at said second end of said indicator unit; and wherein said at least one air-permeable and liquid-impermeable membrane allows bidirectional fluid movement between and through said blood volumeter and said access port.

12. The device of claim 11 further comprising a connector provided in fluid communication with said main tubing segment and wherein said indicator unit is disposed in removable fluid communication with said connector.

13. The device of claim 11 wherein said blood volumeter is a volumeter chamber.

14. The device of claim 11 further comprising a collector conduit provided in fluid communication with said main tubing segment and wherein said indicator unit is disposed in fluid communication with said collector conduit.

15. The device of claim 14 wherein said indicator unit comprises a volumeter conduit provided in fluid communication with said collector conduit and wherein said blood volumeter is provided in fluid communication with said volumeter conduit.

16. The device of claim 15 further comprising a port disposed between said collector conduit and said volumeter conduit.

17. The device of claim 11 further comprising an access port tubing segment provided in fluid communication with said main tubing segment and wherein said access port is provided on said access port tubing segment.

18. The device of claim 11 further comprising a connector provided in said main tubing segment between said clamp and said tubing branch.

19. The device of claim 11 wherein said tubing branch comprises an access port leg and a collector tubing leg communicating with said main tubing segment and wherein said access port communicates with said access port leg and said indicator unit communicates with said collector tubing leg.

* * * * *